US00PP18832P3

(12) United States Plant Patent
Martinez

(10) Patent No.: US PP18,832 P3
(45) Date of Patent: May 27, 2008

(54) PEACH TREE NAMED 'JR 7827'

(50) Latin Name: *Prunus persica*
Varietal Denomination: JR 7827

(76) Inventor: Isidro Martinez, 3031 S. Oak Park St., Visalia, CA (US) 93277

( * ) Notice: Subject to any disclaimer, the term of this patent is extended or adjusted under 35 U.S.C. 154(b) by 6 days.

(21) Appl. No.: 11/445,860

(22) Filed: Jun. 2, 2006

(65) Prior Publication Data

US 2007/0283466 P1 Dec. 6, 2007

(51) Int. Cl.
*A01H 5/00* (2006.01)

(52) U.S. Cl. ..... Plt./198

(58) Field of Classification Search ..... Plt./198
See application file for complete search history.

*Primary Examiner*—Kent Bell
(74) *Attorney, Agent, or Firm*—Mark D. Miller

(57) ABSTRACT

A new and distinct variety that is characterized by producing a freestone fruit with good coloration and that is ripe for commercial harvesting and shipment June 15–25 in the San Joaquin Valley of Central California. The new variety is closely similar to the 'Saucer' peach tree (non-patented) from which it is a bud sport and from which it is distinguishable in that the fruit is much more highly colored, and has yellow flesh.

1 Drawing Sheet

*Prunus persica.*

BACKGROUND OF THE NEW VARIETY

The present invention relates to a new and distinct variety of peach tree (*Prunus persica*) which will hereinafter be denominated varietally as the 'JR 7827' peach and more particularly as a peach tree which produces free stone fruit which can mature for commercial harvest between approximately June 15–25 of each year.

The present invention is a bud sport of a 'Saucer' peach (nonpatented) that was discovered in a 'Saucer' peach planting in the Goshen area of the San Joaquin Valley of Central California in the year 2000. This new variety has the appearance of a 'Saucer' peach as far as the fruit shape (saucer), however it is very highly colored and is yellow fleshed. This bud sport was grafted on a 'Nemaguard' rootstock and planted on the property of the inventor in 2002. By the third year, 2005, the tree had produced a very good crop. The inventor examined the progeny and found that it possessed all the characteristics of the parent.

ORIGIN AND ASEXUAL REPRODUCTION OF THE NEW VARIETY

The present invention (variety) was discovered in a 'Saucer' peach planting at Road 52 and Avenue 320, west of the town of Goshen, Calif. in the year 2000. The new variety was asexually reproduced by bud grafting on 'Nemaguard' rootstock in 2002 on one tree at 3031 South Oak Park Street, Visalia, Calif. 93177. The inventor carefully compared the asexually reproduced tree with the parent sport including the fruit and found they were identical in all respects. The tree described herein is a three year old tree.

SUMMARY OF THE NEW VARIETY

The 'JR 7827' peach is characterized by producing a saucer shaped peach with good blush coloration and is ripe for commercial harvesting and shipment around June 15–June 25 in a normal year in the San Joaquin Valley of Central California as a yellow fleshed, saucer shaped fruit. The new variety of peach is most similar to the 'Saucer' peach (nonpatented) from which it is a bud sport and from which it is distinguishable in that it is more highly colored, has yellow flesh and excellent flavor. The maturity date is at about the same time as the 'Saucer' peach. With good color and excellent flavor, this fruit is markedly quite acceptable to the consumer.

BRIEF DESCRIPTION OF THE DRAWING

The drawing (FIG. 1) is a color photograph of the new variety of peach tree displaying the foliage along the left side and the fruit along the right side. The foliage at the top of the photograph is from a terminal branch, the underside of a leaf is shown in the middle of the photograph next to two fruit pits, and the foliage at the bottom is from an older branch. Along the right side of the photograph, starting at the top, is a top view of a mature fruit, followed by a bottom view of a mature fruit, followed by two suture (side) views of the fruit, followed by a half section of a fruit displaying flesh color and pit well, and ending with the other half section of the fruit displaying the flesh and the pit in the pit well.

DETAILED DESCRIPTION

Figure 1:
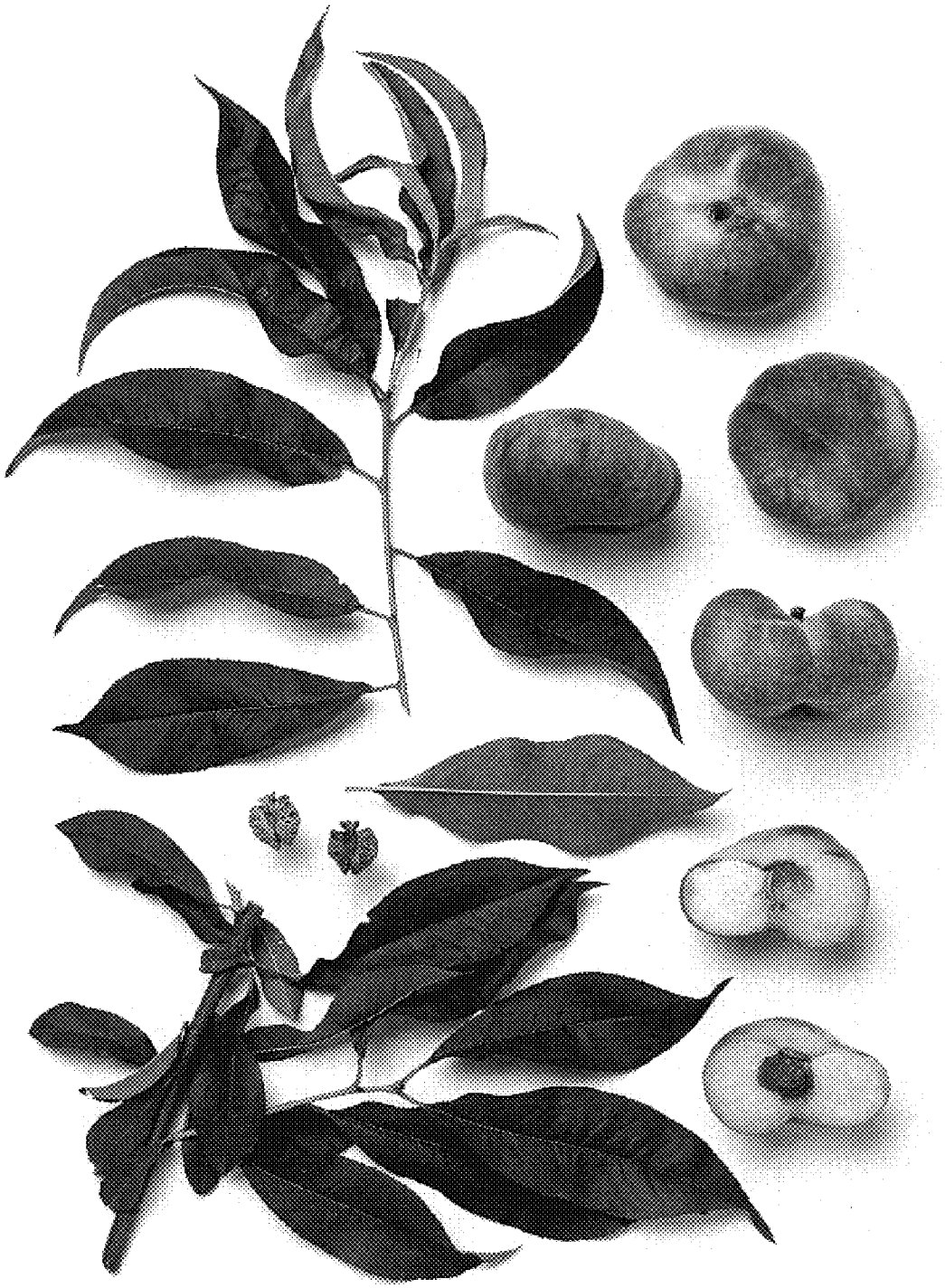

Referring more specifically to the horticultural details of the new and distinct variety of peach tree, the following description has been observed under the ecological conditions prevailing at the origin location which is in the City of Visalia in the San Joaquin Valley of Central California. All major color designations are by reference to the Dictionary of Color by Maera & Paul, First Edition, published in 1930. Common colors are also employed.

TREE

Size—medium—10–11 feet high, 8–9 feet wide.

Vigor—very good at third leaf, with 6–12 inches of new growth.

Chilling requirements—normal for peaches in the San Joaquin Valley of Central California (approx. 800 hours below 45° F.).

Productivity—very good for third leaf tree (comparable to that of fourth leaf trees of other peach varieties).

Regularity of bearing—regular.

Figure—pyramidal—upright and spreading.

Trunk:

*Size.*—Medium — 9 inches in circumference at 12 inches above soil level.

*Surface texture.*—Rough.

*Color code.*—Catawba (56-J-10).

*Lenticels.*—Number—many scattered, 20–25 over a 3-inch square bark surface. Size—11–12 mm (0.43–0.47 inch) on trunk 1 mm (0.04 inch) on branches. Color—(55-H-3) light brown.

Branches:

*Size.*—Medium — 6 inches in circumference at 10 inches above crotch.

*Length.*—Typically 4–5 feet.

*Angle of scaffold branches above the crotch.*—Approximately 63°.

*Surface texture.*—Mature branches—fairly smooth. Immature branches—smooth.

*Color code.*— 1 year or older—Pigeon (55-A-3). Immature—Piquant gr. (20-K-6).

*Lenticels.*—Many, small 1 mm (0.04 inch).

Leaves:

*Size.*—Medium, pinnately veined. Length: 125–132 mm (4.87–5.15 inch). Width: 38–44 mm (1.48–1.72 inch).

*Form.*—Lanceolate.

*Base.*—Cuneate.

*Tip.*—Acuminate.

*Color code.*—Upwardly disposed surface—Empire gr. (23-E-9). Downwardly disposed surface—Near garland gr. (22-H-7).

*Marginal form.*—Serrated.

*Leaf vein.*—Color Code—Fern (21-I-4). Thickness—1 mm (0.04 inch).

*Petiole.*—Size: Length—11–12 mm (0.43–0.47 inch). Thickness—1–2 mm (0.04–0.08 inch). Color Code—Fern (21-I-7). Stem Glands: 0–1 reniform. Color Code—Taupe (16-A-6).

*Glands.*—Size—small—1 mm (0.04 inch). Form—reniform, one on each side of petiole. Color—(20-B-2) Artichoke Gr.

*Stipules.*—Size—one double and one single, 1–2 mm (0.04–0.08 inch). Color Code—tips—Partridge (15-L-2).

FLOWERS

Flower buds:

*Size.*—Length—8–9 mm (0.31–0.35 inch). Width—7–8 mm (0.27–0.31 inch). Height—3 mm (0.12 inch).

Form: conic.

*Color code.*—Vineyard Oporto+ (55-L-12) at base.

Flower:

*Calyx.*—5 sepals with some pubescence on margins and edge. Color Code: Vineyard Oporto+ (55-L-12) at base, Reddish gray (54-F-4).

*Date of bloom.*—February 28: 10–15%. March 6: 95%.

*Size.*—Large when fully opened. Diameter—51–53 mm (1.99–2.07 inches).

*Quantity.*—Abundant, mostly two in a cluster.

*Fragrance.*—None.

*Petals.*—5. Size—generally large. Length—20–23 mm (0.78–0.90 inch). Width—15–17 mm (0.59–0.66 inch). Form—broadly ovate with slightly undulate margins. Color—Peach Blossom (1-C-2) at tip to Spinel R. (3-H-5) on lower half of petal. Apex—rounded. Margin—undulate. Base—tapered. Claws—small—2 mm (0.079 inch) width. Color Code—Jack Rose (3-J-6).

*Pedicels.*—Length—3 mm (0.12 inch). Width—1.5 mm (0.06 inch). Color—midvein: GARNET+ Spanish Wine, Pigeon Blood– (7-J-6).

*Sepals.*—5. Observed shape—narrowly triangular. Margin—entire. Apex—acuminate. Outside surface Color Code—Vineyard Oporto+ (55-L-12). Length—6–7 mm (0.23–0.27 inch). Width—4–5 mm (0.16–0.20 inch).

*Stamens.*—38–40. Length—12–19 mm (0.47–0.74 inch).

*Filaments.*—Color Code—from white (1-B-1) to pink (1-F-2).

*Anthers.*—Color code—Chutney (7-I-12).

*Pistil.*—Length—12 mm (0.47 inch). Color code—Javel gr. (19-L-2).

*Ovary.*—Color Code—Cosse gr. (19-L-6).

Maturity—June 15–25.

Size: Small to medium.

*Diameter in axial plane.*—40 mm (1.56 inches).

*Transverse in suture plane.*—70 mm (2.73 inches).

*Transverse at right angles to suture plane.*—68 mm (2.65 inches).

Form:

*Uniform.*—Not uniform.

*Symmetrical or not symmetrical.*—Symmetric — saucer shape.

*Suture.*—Faint.

*Ventral surface.*—Smooth.

*Stem cavity.*—Width—12 mm (0.47 inch). Length—2.5 mm (0.10 inch). Depth—10 mm (0.39 inch). Form—ovate.

*Stem length.*—Short — 5 mm (0.20 inch).

*Stem color.*—(20-J-4) near Absinthe Gr.

*Apex.*—None.

*Pistil point.*—None.

*Caliper.*—4 mm (0.16 inch).

Skin:

*Thickness.*—Thin.

*Texture.*—Firm.

*Tendency to crack.*—Not known.

*Color code.*—Blush—Pansy Pr. (54-L-8). Ground Color—March Rose (5-I-9). Flesh Color—Apricot Y (9-K-5) and on one side of flesh Off White (3-A-7). Surface of Pit Cavity—Apricot Y (9-K-5). Pit Well—Raspberry (6-I-5).

Flesh:

*Juice production.*—Very good.

*Flavor.*—Very good.

*Aroma.*—Moderate.

*Texture.*—Slightly firm to soft.

*Fibers.*—Few.

*Ripening.*—Even.

*Eating quality.*—Very good to excellent.

Use—fresh market.

Keeping & shipping quality—short term.

Resistance to disease—not known.

Harvesting—June 15–25.

STONE

Free or cling—Free.
Fibers:
*Numbers.*—Numerous.
*Length.*—10–13 mm (0.39–0.51 inch).
Size:
*Length.*—11–14 mm (0.43–0.55 inch).
*Width.*—17–23 mm (0.57–0.91 inch).
*Thickness.*—12–14 mm (0.47–0.55 inch).
Form—oval — flat to slightly rounded at both apex and base.
Apex shape—flat to slightly rounded.
Color dry—Wild Cherry (6-C-6).
Base—flat to slightly rounded.
Sides—even but heavily pitted.
Hilium—3–5 mm (0.12–0.195 inch).
Ridges—on ventral side narrower than on distal side, from base to apex.
Tendency to split—none observed.

Having thus described and illustrated my new variety of peach tree which I claim as new and desire to be secured by plant Letters Patent is:

1. A new and distinct variety of peach tree as described herein that is somewhat similar to the 'Saucer' peach tree from which it is a bud sport, but from which it is distinguished therefrom in that the fruit is more highly colored, has yellow flesh and which is ready for commercial harvesting and shipment about June 15–25 of each year.

* * * * *